United States Patent [19]

Eidt

[11] 4,155,926

[45] May 22, 1979

[54] COMPOUNDS

[75] Inventor: Scott H. Eidt, Seabrook, Tex.

[73] Assignee: Texas Alkyls, Inc., Deer Park, Tex.

[21] Appl. No.: 576,481

[22] Filed: May 12, 1975

Related U.S. Application Data

[63] Continuation of Ser. No. 496,678, Aug. 12, 1974, abandoned.

[51] Int. Cl.$^2$ .............................................. C07F 5/06
[52] U.S. Cl. ............................ 260/448 A; 252/431 R; 252/433
[58] Field of Search .................................. 260/448 A

[56] References Cited

U.S. PATENT DOCUMENTS

| | | | |
|---|---|---|---|
| 3,509,189 | 4/1970 | Ort et al. | 260/448 A |
| 3,509,190 | 4/1970 | Ort et al. | 260/448 A |
| 3,577,450 | 5/1971 | Ort et al. | 260/448 A |
| 3,700,710 | 10/1972 | Mottus et al. | 260/448 A |
| 3,910,979 | 10/1975 | Eidt | 260/448 A |

FOREIGN PATENT DOCUMENTS 1264443  3/1968  Fed. Rep. of Germany.

OTHER PUBLICATIONS

Chemical Abstracts 58, 10307f (1963).
Kooyman et al., Tetrahedron Letters, No. 12, pp. 24–27 (1959).
Lehmkuhl et al., Tetrahedron Letters, No. 21, pp. 2315–2320 (1966).

*Primary Examiner*—Helen M. S. Sneed
*Attorney, Agent, or Firm*—Michael J. Bradley

[57] ABSTRACT

Novel organoaluminum compounds having the general formula:

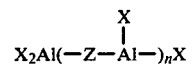

wherein Z is (—CH$_2$CH$_2$—); X is chloro-, bromo-, or iodo-, and n is 1, except that when X is chloro-, n is a number from 2 to 20, are disclosed. The compounds are prepared by reacting aluminum metal with an anhydrous aluminum trihalide and ethylene. The compounds are useful as co-catalysts for Ziegler polymerizations.

3 Claims, No Drawings

COMPOUNDS

This is a continuation of application Ser. No. 496,678, filed Aug. 12, 1974, now abandoned.

BACKGROUND OF THE INVENTION

Organoaluminum compounds containing dialuminoalkane grousp($>$Al—R—Al$<$) are known. Oligomeric aluminum methylene compounds and bis(dichloroaluminum) methane have been made by reaction of aluminum metal with methylene chloride as shown in the following equation given by Lehmkuhl and Schafer, *Tetrahedron Lett.*, No. 21, 2315 (1966):

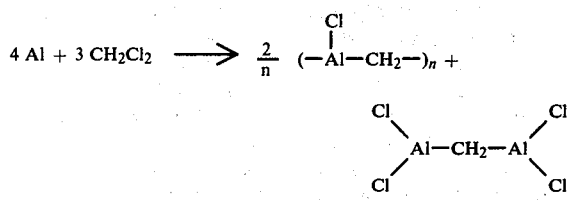

The authors used these compounds as co-catalysts for olefin polymerization procedures, such as those described in German Pat. No. 1,264,443.

1,2-Bis(dichloroaluminum)ethane has been prepared by reduction of aluminum chloride with potassium in the presence of ethylene according to the following equation from Kooyman et al., *Tetrahedron Lett.*, No. 12, 24 (1959):

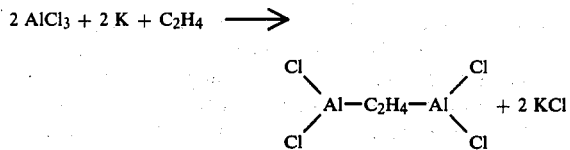

They obtained the compound described above as the diethyl ether complex, Al$_2$Cl$_4$C$_2$H$_4$.2Et$_2$O. Though the authors did not isolate the ether-free compound, they suggested that this compound was the active co-catalyst with TiCl$_4$ in some ethylene polymerization tests which they performed. Compounds closely related to the present invention are also described in German Pat. No. 2,236,193.

SUMMARY OF THE INVENTION

This invention comprises novel halogenated dialuminumethanes having the general formula:

$$X_2Al(-Z-\underset{\underset{X}{|}}{Al}-)_nX$$

wherein X is chloro-, bromo-, or iodo-, Z is —CH$_2$CH$_2$—, and n is 1, except that when X is chloro-, n is a number from 2 to 20, and a method of preparation of these compounds. In its preferred form, the invention comprises compounds of the formula indicated wherein X is chloro- or bromo-.

DETAILED DESCRIPTION OF THE INVENTION

According to the invention, an aluminum trihalide is allowed to react with aluminum metal and ethylene. The aluminum trihalide must be anhydrous, but not necessarily of high purity, and can be in the form of powder or any of the commercial forms available. The aluminum metal, which can be any of the finely divided forms commercially available, is activated in situ in the presence of the aluminum trihalide, and no special chemical activator or milling is required. The bridging group may be defined as the ethylene radical to which aluminum is bonded in the 1,2-positions.

In the preferred embodiment of the process, powdered aluminum is slurried with a solution or suspension of aluminum trihalide and brought to reaction temperature. Ethylene is introduced into the reactor either beneath the liquid or into the vapor space above the liquid at a pressure sufficient to keep a substantial portion of the olefin dissolved in the liquid. The temperature should be as low as practical for reasonable rates to prevent undesired side reactions and preferably should be in the range of 50°–150° C. The required pressure may vary, but in general, it should be as low as possible to prevent side reactions. Pressures in the range of 1–10 atmospheres are preferred, although pressures up to 50 atmospheres may be used. The reaction is continued, with stirring, until olefin consumption ceases or until the desired composition is attained. The reaction rate is conveniently followed by observing the pressure drop when ethylele feed is interrupted.

The solvent or suspension medium of choice is an alkyl, cycloalkyl, or alkylcycloalkyl hydrocarbon, preferably containing from 4 through 12 carbon atoms. A cycloparaffinic solvent, methylcyclohexane, was used in the reactions described in the examples below because of the increased solubility of the aluminum trihalide in this liquid. When a cyclohexane is used, care must be taken to exclude traces of moisture that catalyze isomerization of the cyclohexane ring to methylcyclopentane. Aromatic hydrocarbon solvents should be avoided because of possible alkylation reactions. In general, the reaction product will precipitate as a solid from the hydrocarbon solvent. The solid product can be separated from the unreacted aluminum metal by conventional techniques. For example, the separation can be effected by decanting the hydrocarbon and dissolving the product in a liquid alkylaluminum compound. If isolation of the pure solid product is desired, it can be reprecipitated by adding the organoaluminum solution to a hydrocarbon. The compounds are useful as co-catalysts for Ziegler polymerizations.

The product from AlCl$_3$, Al, and ethylene has an appreciable solubility in hydrocarbons whereas the corresponding AlBr$_3$ reaction product is relatively insoluble. The difference in solubility of these compounds may be related to the oligomeric structure of the chloride-containing product. The reaction involving AlBr$_3$ ceases abruptly when the stoichiometric quantity of ethylene required for the monomer is consumed, for example:

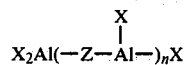
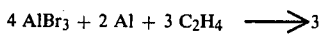
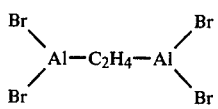

In the case of the AlCl$_3$ reaction, the volume of the solid product increased to a maximum as the stoichiometric quantity of olefin (3 moles olefin per 4 moles AlCl$_3$) was approached, but as excess olefin was added, the reaction continued and the volume of solid was reduced as if it were dissolving. Analysis of the final solution gave a Cl/Al atomic ratio less than 2 which showed that the product was oligomeric.

The following examples are presented to demonstrate this invention but are not intended to limit the scope thereof.

EXAMPLE I

Each reaction described was conducted in a heavy-walled pyrex bottle (Fischer and Porter 12-oz. aerosol tube) fitted with an adjustable diptube, which permitted gas entry either into the vapor space of beneath the liquid. The head assembly also included a pressure gauge and a pressure relief valve. The bottle was charged with 40 g. (1.48 g. atoms) of powdered aluminum (30–325 mesh) and 98 g. (0.37 mole) of anhydrous aluminum tribromide under an atmosphere of dry nitrogen. The bottle was capped and 120 g. of methylcyclohexane was transferred into the bottle via the diptube. The bottle was placed into an oil bath at 90° C. for 30 minutes prior to adding ethylene, during which time the aluminum tribromide completely dissolved. The reaction began immediately upon the addition of ethylene into the vapor space. The slurry was vigorously stirred with a magnetic stirring bar as ethylene was fed on demand at 30 psig. After 1½ hours, the reaction ceased abruptly as evidenced by no additional pressure drop. The reaction consumed 7.8 g. (0.28 mole) of ethylene or almost exactly the stoichiometric amount required for formation of 1,2-bis(dibromoaluminum)ethane. The voluminous, gray solid product was almost indistinguishable from the unreacted aluminum, but the total solids volume was about four times that of the initial aluminum. After the solids had settled, the hydrocarbon solution was slightly yellow.

Analysis of the hydrocarbon solution showed an aluminum content of 0.28%, indicating complete conversion of aluminum bromide to an insoluble product. A sample of the product slurry was centrifuged in a sealed vial and the solvent was decanted. The residual solid was washed with hexane, dried, and weighed. A known weight of trimethylaluminum was added to the solid to dissolve the product. The remaining unreacted aluminum was washed with hexane, dried, and weighed. Upon analysis and appropriate calculations to compensate for the solvent contribution, the product was found to contain 13.14% Al and 79.82% Br for a Br/Al ratio of 2.05. The hydrolysis gas contained 5.45 mole % ethane compared to 5.21% expected from the hydrolysis gas of the trimethylaluminum solution. Analysis of the trimethylaluminum solution of the product by nmr verified the 1,2-dialuminoethane structure.

EXAMPLE II

The bottle reactor described in Example I was charged with 40 g. (1.48 g. atoms) of powdered aluminum and 87 g. (0.65 mole) of anhydrous aluminum trichloride powder. Methylcyclohexane (139 g.) was transferred into the bottle and the reactor was placed into an oil bath at 95° C. Ethylene was fed on demand into the vapor space at 30 psig. After about 6½ hours the reaction was interrupted for inspection. Ethylene consumption at this stage was 16.2 g. (0.58 mole). After settling overnight about 10% of the mixture was an orange solution above the gray solid suspension. On being heated, the thick slurry could be stirred. Ethylene feed was continued for about 3½ hours until the magnetic stirring bar would not function, but even at this time ethylene was still being consumed. The resulting mixture was a gray solid below a transparent, dark red solution. The volume of the final solid was only about one-third of the maximum solids volume attained. The total ethylene consumed during the run was 23 g. (0.82 mole) indicating that the reaction went beyond the monomer to form oligomeric product.

Analysis of the hydrocarbon solution gave 5.92% aluminum and 13.70% chloride for a Cl/Al ratio of 1.76. The Cl/Al ratio of less than 2.0 verified that oligomeric product was formed. A diethyl ether solution of the solid product was found to contain 10.76% aluminum and 25.57% chloride for a Cl/Al ratio of 1.81. The solid was dissolved in triisobutylaluminum and the hydrolysis gas analysis of the solution confirmed the presence of ethane.

EXAMPLE III

The bottle reactor described in Example I is charged with 40 g. (1.48 g. atoms) of powdered aluminum and 150 g. (0.37 mole) of anhydrous aluminum triiodide. Methylcyclohexane (150 g.) is transferred into the bottle and the reactor is placed into an oil bath at 95° C. for 30 minutes prior to adding the olefin. Ethylene is fed on demand into the vapor space at 30 psig. The mixture is stirred until ethylene consumption ceases. The product is recovered by conventional techniques.

As indicated, the compounds are useful as cocatalysts in Ziegler polymerizations. The compounds may be employed, for example, in the manner described in German Pat. No. 1,264,443, or in the manner described in *Tetrahedron Lett.*, No. 12, 24 (1959).

I claim:

1. A method for the production of a compound having the formula

wherein X is chloro-, bromo-, or iodo- and n is 1, except that when X is chloro-, n is a number from 2 to 20, comprising, reacting an anhydrous aluminum trihalide (AlX$_3$) with aluminum and ethylene in a hydrocarbon solvent.

2. The method of claim 1 wherein the reacting step is conducted at a temperature from 50°–150° C. and at a pressure of from 1–10 atomspheres in a solvent selected from the group consisting of alkyl, cycloalkyl of alkylcycloalkyl hydrocarbon solvents.

3. The process of claim 2 wherein the hydrocarbn solvent contains from 4 to 12 carbon atoms.